(12) United States Patent
Cotter et al.

(10) Patent No.: US 6,498,194 B2
(45) Date of Patent: Dec. 24, 2002

(54) FUNGICIDAL MIXTURES

(75) Inventors: Henry Van Tuyl Cotter, Trenton, NJ (US); Gunther Reichert, Bubenheim (DE); Ewald Sieverding, Johann (DE); Petrus Martinus Franciscus Emanuel Jegerings, Wavre (BE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/046,190

(22) Filed: Jan. 16, 2002

(65) Prior Publication Data

US 2002/0099062 A1 Jul. 25, 2002

Related U.S. Application Data

(63) Continuation of application No. 09/240,412, filed on Jan. 29, 1999, now Pat. No. 6,346,535.

(51) Int. Cl.$^7$ ............... A01N 35/00; A01N 43/54; A01N 43/48; A01N 37/12; A01N 37/44
(52) U.S. Cl. ............... 514/687; 424/638; 514/237.5; 514/272; 514/275; 514/276; 514/352; 514/388; 514/417; 514/433; 514/434; 514/520; 514/524; 514/538; 514/634; 514/648
(58) Field of Search ............... 514/687, 275, 514/634, 648, 237.5, 272, 276, 352, 388, 417, 433, 434, 520, 524, 538; 424/638

(56) References Cited

U.S. PATENT DOCUMENTS

5,922,905 A * 7/1999 Curtze et al. ............... 562/474
5,945,567 A * 8/1999 Curtze et al. ............... 568/333

\* cited by examiner

Primary Examiner—Allen J. Robinson
(74) Attorney, Agent, or Firm—Keil & Weinkauf

(57) ABSTRACT

The invention relates to a novel fungicidal composition comprising a fungicidally acceptable carrier and/or surface active agent together with, and synergistically effective amounts of
(a) at least one benzophenone of formula I

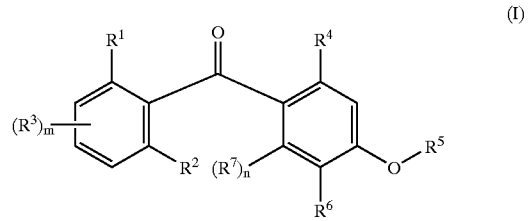

wherein $R^1$, $R^2$, $R^3$, $R^4$, $R^5$, $R^6$, $R^7$, m and n have the meaning given;
at least one fungicidal active ingredient selected from the following groups (A), (B), (C), (D) and (E):
(A) an ergosterol biosynthesis inhibitor;
(B) a strobilurine derivative,
(C) a melanin biosynthesis inhibitor;
(D) a compound selected from the group consisting of acibenzolar, benomyl, captan, carboxin, chlorothalonil, copper, cyprodinil, dinocap, dithianon, dimethomorph, dodine, ethirimol, famoxadone, fenpiclonil, fluazinam, mancozeb, metalaxyl, pyrifenox, sulfur, vinclozolin and
(E) an azolopyrimidine of formula II

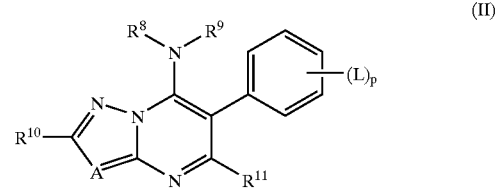

in which $R^8$, $R^9$, $R^{10}$, $R^{11}$, A, L and p have the meaning given;
and to a method of controlling the growth of phytopathogenic fungi at a locus which comprises applying synergistically effective amounts of (a) at least one benzophenones of formula I and (b) at least one fungicidal active ingredient selected from the groups (A), (B), (C), (D) and (E) to the locus.

14 Claims, No Drawings

FUNGICIDAL MIXTURES

CROSS REFERENCE TO RELATED APPLICATION(S)

This is a Continuation application of U.S. application Ser. No. 09/240,412, filed Jan. 29, 1999, now U.S. Pat. No. 6,346,535 B1.

BACKGROUND OF THE INVENTION

The present invention relates to a fungicidal composition comprising a fungicidally acceptable carrier and/or surface active agent and synergistically effective amounts of (a) at least one benzophenone of formula I

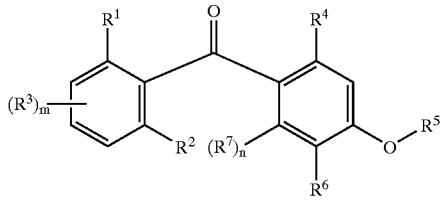

wherein
$R^1$ represents a halogen atom, an optionally substituted alkyl, alkanoyloxy or alkoxy group; or a hydroxy group,
$R^2$ represents a halogen atom or an optionally substituted alkyl group,
m is 0 or an integer of 1 to 3;
$R^3$ independently represents a halogen atom, an optionally substituted alkyl or alkoxy group or a nitro group;
$R^4$ represents a halogen atom, a cyano, carboxy, hydroxy or nitro group or an optionally substituted alkyl, alkoxy, alkenyl, alkylthio, alkylsulphinyl, alkylsulphonyl or amino group;
$R^5$ represents an optionally substituted alkyl group;
$R^6$ represents a halogen atom or a nitro group, an optionally substituted alkyl, alkoxy, alkenyloxy, alkynyloxy, alkylthio, cycloalkyl, cycloalkyloxy, aryloxy group;
n is 0 or 1; and
$R^7$ independently represents a halogen atom, an optionally substituted alkyl, alkenyl, alkynyl, alkoxy, alkenyloxy, alkynyloxy, cycloalkyl, cycloalkoxy group;
(b) at least one fungicidally active ingredient selected from the following groups (A), (B), (C), (D) and (E):
(A) an ergosterol biosynthesis inhibitor;
(B) a strobilurine derivative,
(C) a melanin biosynthesis inhibitor,
(D) a compound selected from the group consisting of acibenzolar, benomyl, captan, carboxin, chlorothalonil, copper, cyprodinil, dinocap, dithianon, dimethomorph, dodine, ethirimol, famoxadone, fenpiclonil, fluazinam, mancozeb, metalaxyl, pyrifenox, sulfur and vinclozolin, and (E) an azolopyrimidine of formula II

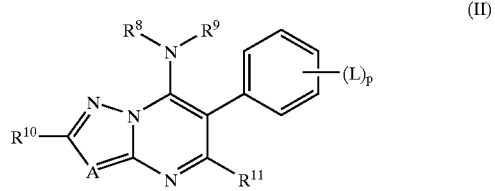

in which
$R^8$ and $R^9$ each independently represent hydrogen or an optionally substituted alkyl, alkenyl, alkynyl, alkadienyl, aryl, heteroaryl, cycloalkyl, bicycloalkyl or heterocyclyl group, or
$R^8$ and $R^9$ together with the interjacent nitrogen atom represent an optionally substituted heterocyclic ring,
$R^{10}$ represents hydrogen or an alkyl or aryl group,
$R^{11}$ represents a hydrogen or halogen atom or an alkyl or alkoxy group,
L independently represents a halogen atom or an optionally substituted alkyl or alkoxy group,
A represents N or $CR^{12}$, wherein $R^{12}$ has the meaning given for $R^{10}$, and
is 0 or an integer from 1 to 5.

The fungicidal compounds of formula I to be used according to the present invention are known for example from U.S. Pat. No. 5,773,663.

The compounds of the classes (A), (B) and (D) are known from The Pesticide Manual 11$^{th}$ edition 1997, Editor Clive Tomlin.

The class of melanin biosynthesis inhibitors (MBI) (C) are chemical compounds which are capable of diminishing the in-vivo synthesis of melanin by inhibiting any of the reductase and/or dehydratase enzymes which are responsible for converting tetrahydroxynaphthalene into dihydroxynaphthalene. This class of compounds includes the following known compounds: carpropamid, chlobenthiazione, diclocymet, pyroquilon, phthalide, tricyclazole and certain phenoxyamides, which are known for example from EP 0 262 393, in particular AC 382042 and Japanese patent application JP 5-9165-A.

The fungicidal compounds of formula 11 to be used according to the present invention are known for example from U.S. Pat. No. 5,593,996 and from International patent applications WO 98/46607 and WO 98/46608.

U.S. Pat. No. 5,773,663 suggests to combine fungicidal benzophenone derivatives with other fungicides such as 4,6-dinitro-o-cresol, benalaxyl, benomyl, captafol, captan, carbendazim, chlorothalonil, copper, cymoxanil, dichlofluanid, dichlone, difenoconazole, dimethomorph, diniconzole, dinocap, dithianon, fenpiclonil, fenpropiomorph, hymaxazol, imazalil, iprodione, isoprothiolane, kasugamycin, mancozeb, mepronil, mercuric oxide, oxadixyl, oxolinic acid, penconazole, propineb, pyrifenox, thiabendazole, thiram, tolclofos-methyl, triadimefon, triflumizole, triforine validamycin A, vinclozolin, zineb and ziram.

However, there is no hint that such mixtures show synergistic effects and can advantageously be used for controlling diseases such as wheat powdery mildew, wheat leaf rust and wheat Septoria leaf blotch, Botrytis diseases and others.

Surprisingly, a strong synergy between the compounds of formula I and the fungicidally active ingredients selected from the classes (A), (B), (C), (D) and (E) as described above in greenhouse and field trials was found when these two compounds were in-tank mixed and when the activity of these mixtures was compared with that of the solo activity of each active ingredient.

A mixture of fungicides shows synergistic effect if the fungicidal activity of the mixture is larger than the sum of activities of the separately applied compounds. The expected fungicidal activity for a given mixture of two fungicides can also be calculated as follows (See Colby, S. R., "Calculating synergistic and antagonistic response of herbicide combinations", Weeds 15, pp 20–22 (1967):

$$E = X + Y - \frac{XY}{100}$$

wherein x is the efficacy in % compared with an untreated control upon treatment with a fungicidal active ingredient A at a dose rate a;

y is the efficacy in % compared with an untreated control upon treatment with a fungicidal active ingredient B at a dose rate b;

EE is the expected efficacy with a combination of fungicidal active ingredients A and B at a dose of a+b, respectively.

If the actual efficacy (E) exceeds the expected (calculated) one (EE), the mixture displays a synergistic effect.

SUMMARY OF THE INVENTION (b) The present invention includes a fungicidal composition comprising an acceptable carrier and/or surface active agent and synergistically effective amounts of at least one compound of formula I, and at least one fungicidal active ingredient selected from the following the following groups (A), (B), (C), (D) and (E):

(A) an ergosterol biosynthesis inhibitor;
(B) a strobilurine derivative,
(C) a melanin biosynthesis inhibitor,
(D) a compound selected from the group consisting of acibenzolar (BION), benomyl, captan, carboxin, chlorothalonil, copper, cyprodinil, dinocap, dithianon, dimethomorph, dodine, ethirimol, famoxadone, fenpiclonil, fluazinam, mancozeb, metalaxyl, pyrifenox, sulfur and vinclozolin, and
(E) an azolopyrimidine of formula II.

The present invention also includes a method of controlling the growth of phytopathogenic fungi at a locus which comprises applying synergistically effective amounts of at least one benzophenone of formula I and at least one fungicidally active ingredient selected from the following classes (A), (B), (C), (D) and (E) as defined above to the locus.

DETAILED DESCRIPTION OF THE PREFERRED EMBODIMENTS

Preferred compounds of formula I are benzophenones of formula IA,

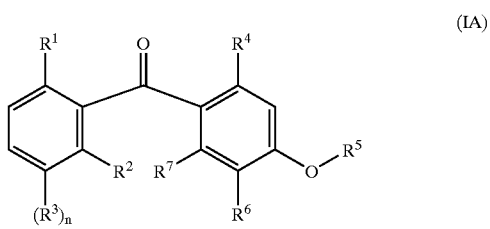

(IA)

wherein $R^1$ represents a halogen atom, a methyl, trifluoromethyl, methoxy or hydroxy group, in particular a chlorine atom, a methyl or methoxy group;

$R^2$ represents a halogen atom, in particular a chlorine atom or a methyl group;

$R^3$ represents a bromine or chlorine atom, a methyl, trifluoromethyl or nitro group, in particular a bromine atom;

$R^4$ represents a methyl group;

$R^5$ represents an alkyl group, in particular a methyl group;

$R^6$ and $R^7$ each independently represent an alkoxy group which may be substituted by a phenyl, alkylphenyl or halophenyl group, preferably C1–6 alkoxy being optionally substituted by a phenyl, methylphenyl or fluorophenyl group, in particular methoxy, benzyloxy and 2-fluorobenzyloxy; and n is 0 or 1.

Particularly preferred are the benzophenones selected from the group consisting of 6'-butoxy-2,6-dichloro-4',5'-dimethoxy-2'-methylbenzophenone coded BP-1, 2,6-dichloro-4',5'-dimethoxy-6'-(2-fluorobenzyloxy)-2'-methylbenzophenone coded BP-2, 6'-benzyloxy-4',5'-dimethoxy-2,6-dimethyl-2'-methylbenzophenone coded BP-3; 5-bromo-2',6-dimethyl-2,4',5',6'-tetramethoxybenzophenone coded BP-4 and 2,6-dichloro-2'-methyl-4',5',6'-trimethoxybenzophenone coded BP-5, most preferred is BP-4.

Preferred ergosterol biosynthesis inhibitors of group (A) are selected from the group consisting of fenarimol, fenpropimorph, fenpropidine, spiroxamine and triforine.

Another group of ergosterol biosynthesis inhibiotors are azole derivatives of formulae IIIA and IIIB,

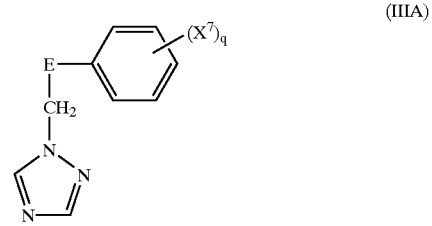

(IIIA)

wherein

E represents a linking group selected from the groups (a), (b), (c), (d) and (e):

(a)

-continued

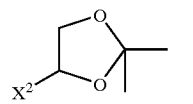
(b)

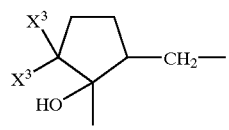
(c)

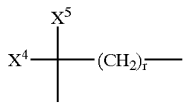
(d)

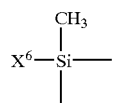
(e)

in which $X^1$ represents an alkyl or an optionally substituted phenyl group;

$X^2$ and $X^3$ each independently represent a hydrogen atom or an alkyl group;

$X^4$ represents an alkyl or cyclopropylalkyl group;

$X^5$ represents a hydroxy or cyano group;

$X^6$ represents an optionally substituted phenyl group;

$X^7$ represents a halogen atom;

q is 1, 2 or 3; and r is 0 or 2;

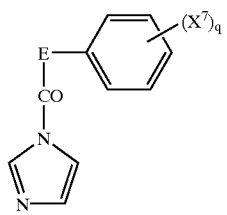
(IIIB)

wherein $X^7$ and q have the meaning given for formula IIIA, and

E represents a group of formula —N($X^8$)—($CH_2$)$_s$—O—, in which $X^8$ represents a hydrogen atom or an alkyl group and s is an integer from 1 to 6.

Particularly preferred azole derivatives of group (A) are selected from the group consisting of cyproconazole, epoxiconazole, flusilazole, metconazole, myclobutanil, penconazole, prochloraz, propiconazole, tebuconazole, triadimefon and tridimenol. Most preferred are epoxiconazole, metconazole, myclobutanil and prochloraz.

Preferred strobilurine derivatives of group (B) are the compounds of formula IV,

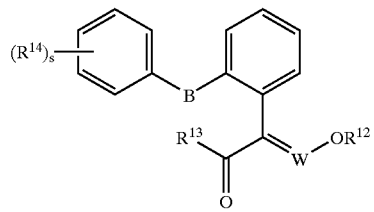
(IV)

wherein

W represents N or CH;

B represents a —O—, —OCH$_2$—, a —CH$_2$O—, a pyrimid-4,6-dioxydiyl group or a group of formula

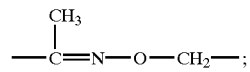

$R^{12}$ represents a $C_{1-4}$ alkyl group;

$R^{13}$ represents a $C_{1-6}$ alkoxy or a $C_{1-6}$ alkylamino group;

$R^{14}$ represents a hydrogen or halogen atom or a cyano, a $C_{1-4}$ alkyl or a $C_{1-4}$ haloalkyl group; and s is 0, 1 or 2;

in particular azoxystrobin, kresoxim methyl, trifloxystrobin or SSF126, most preferred azoxystrobin and kresoxim methyl.

Preferred melanin inhibitors of group (C) are selected from the group consisting of capropamid, chlobenthiazone, diclocymet, pyroquilon, phthalide, tricyclazole and a phenoxamide coded AC 382042, most preferred is AC 382042.

Preferred compounds of group (D) are selected from the group consisting of acibenzolar (BION), cyprodinil, dodine, ethirimol, famoxadone, fenpiclonil, fluazinam, mancozeb and metalaxyl.

Preferred azolopyrimidines of group (E) are the compounds of formula IIA,

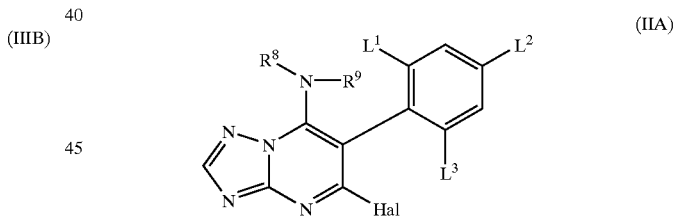
(IIA)

wherein $R^8$ represents a $C_{1-8}$ alkyl, $C_{2-8}$ alkenyl, $C_{3-8}$ cycloalkyl or $C_{1-8}$ haloalkyl group, in particular a straight-chained or branched $C_{3-6}$ alkyl, $C_{2-6}$ alkenyl, $C_{5-6}$ cycloalkyl or $C_{2-6}$ fluoroalkyl group, most preferred an isopropyl, 2-butyl, cyclopentyl, methallyl, 2,2,2-trifluoroethyl or 1,1,1-trifluoroprop-2-yl group; and $R^9$ represents a hydrogen atom, or a $C_{1-8}$ alkyl group; most preferred a hydrogen atom or a methyl or ethyl group; or $R^8$ and $R^9$ together form an optionally substituted alkylene group having 3 to 6 carbon atoms in the main chain, in which one $CH_2$ group may be replaced by O, S or NH, in particular a piperid-1-yl group being optionally substituted by a $C_{1-6}$ alkyl group, most preferred a 4-methylpiperid-1-yl group;

$L^1$, $L^2$ and $L^3$ each independently represent a hydrogen or halogen atom or a $C_{1-4}$ alkoxy group, at least one of which represents a halogen atom, in particular wherein $L^1$ represents a fluorine atom, $L^2$ represents a hydrogen or fluorine atom or a methoxy group and $L^3$ represents a fluorine or chlorine atom; and Hal denotes a halogen atom, in particular a chlorine atom. Particularly preferred are the azolopyrimidines of formula 11 selected from the group consisting of 5-chloro-6-(2-chloro-6-fluorophenyl)-7-(cyclopropylamino)-[1,2,4]triazolo[1,5-a]pyrimidine coded AP-1, 5-chloro-6-(2-chloro-6-fluorophenyl)-7-(4-methylpiperid-1-yl)-[1,2,4]triazolo[1,5-a]pyrimidine coded AP-2, 5-chloro-6-(2-chloro-6-fluorophenyl)-7-(2,2,2-trifluoroethylamino)-[1,2,4]triazolo[1,5-a]pyrimidine coded AP-3 and 5-chloro-6-(2,4,6-trifluorophenyl)-7-[2-(1,1,1-trifluoro)propylamino]-[1,2,4]triazolo[1,5-a]pyrimidine coded AP-4, most preferred is AP-4.

A particularly preferred embodiment of this invention are compositions of three active ingredients which comprise one compound of formula I and two different compounds selected from the groups (A), (B), (C), (D) and (E), preferably one strobilurine compound selected from group (B) and one ergosterol biosynthesis inhibitor of group (A), in particular kresoxim-methyl and epoxiconazole or kresoxim-methyl and fenpropimorph.

Another particularly preferred embodiment of the invention are compositions comprising one compound of formula I and two different compounds of group (D), in particular dimethomorph and mancozeb.

Preferred are co-formulations, comprising the following constituents:

a carrier;

at least one benzophenone of formula I, at least one compound selected from the classes (A) through (E) as defined above;

optionally an adjuvant selected from the group consisting of polyalkoxylated alcohols, triglycerides and amines, in particular Synperonic 91-6, which is commercially available from Uniqema, formerly ICI Surfactants;

optionally a foam breaking agent.

The compound of formula I and the compound selected from the classes (A) through (E) as defined above are to be applied together, in synergistically effective amounts. These synergistic mixtures exhibit an extraordinary efficacy against a broad range of phytopathogenic fungi, in particular against fungi from the classes ascomycetes, basidiomycetes, oomycetes and deuteromycetes. Therefore, they can be applied advantageously against a broad range of diseases in different crops. They may be applied as leaf, stem, root, into-water, seed dressing, nursery box or soil fungicides.

The mixture according to the invention may be preferably applied for controlling phytopathogenic fungi of the genera: Achlya, Altemaria, Balansia, Bipolaris, Blumeria, Botrytis, Cercospora, Cochliobolus, Curvularia, Cylindrocladium, Drechslera, Entyloma, Erysiphe, Fusarium, Gaeumannomyces, Gerlachia, Gibberella, Guignardia, Leptosphaeria, Magnaporthe, Mucor, Mycosphaerella, Myrothecium, Nigrospora, Peronospora, Phoma, Pseudoperonospora, Pseudocercosporella, Phytophthora, Puccinia, Pyrenophora, Pyricularia, Pythium, Rhizoctonia, Rhizopus, Rhynchosporium, Sarocladium, Sclerophthora, Sclerotium, Septoria, Tilletia, Uncinula, Ustilago, Ustilaginoidea, and Venturia, in particular the species *Blumeria graminis f.* sp. *tritici, Cercospora beticola, Septoria tritici, Erysiphe cichoracearum, Puccinia recondita* and *Pyrenophora teres*. The mixtures according to the invention are in particular applied for controlling the above phytopathogenic fungi on monocotylydoneous plants, such as barley and wheat, rice and turf grases or fruit crops such as pomefruits, stonefruits and vines as well as all kinds of vegetables and ornamentals.

The application rate of the compound of formula I according to this invention is usually in the range of 1 to 2000 grams of active ingredient (g a.i.) per hectare, with rates between 20–500 g a.i./ha often achieving satisfactory control. The optimal rate for a specific application will depend on the crop(s) under cultivation and the predominant species of infesting fungi, and readily may be determined by established biological tests known to those skilled in the art.

In general, the preferred application rate of the compounds of formula I is in the range of 10 to 500 g a.i./ha, preferably 20–300 g a.i./ha.

The optimal rate for the compound of group (b) including the classes (A) through (E) will, however, depend on the crop(s) under cultivation and the level of infestation by the fungus, and can readily be determined by established biological tests.

The ratio (by weight) of the compound of formula I to the fungicidal active ingredient of the classes (A) through (E) as defined above is as a rule, from 100:1 to 1:100. The preferred ratio formula I: (A) through (E) may vary, e.g., from about 10:1 to about 1:10, in particular from about 5:1 to about 1:5, most preferred from 2:1 to 1:2.

In the three-ways-compositions according to the present invention, i.e. the compositions containing one compound of formula I and two different compounds selected from the classes (A) through (E), the preferred relative ratios (by weight) are as follows:

compound of formula I: 200 to 1, preferably 20 to 1

1st compound of (A) to (E): 1 to 100, preferably 1 to 10

2nd compound of (A) to (E): 1 to 100, preferably 1 to 10.

The active compounds can be co-formulated together in a suitable ratio according to the present invention, together with usual carriers or diluents and/or additives known in the art.

Accordingly the invention further provides a fungicidal composition which comprises a carrier and, as active ingredient, at least one compound of formula I as defined above and at least one fungicidal active ingredient selected from the classes (A) through (E) as defined above.

A method of making such a composition is also provided which comprises bringing the compound of formula I and the fungicidal active ingredient selected from the classes(A) through (E) as defined above into association with at least one carrier. It is also envisaged that different isomers or mixtures of isomers of formula I and/or the fungicidal active ingredient selected from the classes (A) through (E) may have different levels or spectra of activity and thus compositions may comprise individual isomers or mixtures of isomers.

A composition according to the invention preferably contains from 0.1% to 99.9%, preferably 0.2 to 80% by weight (w/w) of active ingredients.

A carrier in a composition according to the invention is any material with which the active ingredient is formulated to facilitate application to the locus to be treated, which may be for example be a plant, seed, foliage, soil, or into the water where the plant grow, or to the roots or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, tablets, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid auxilaries and/or adjuvants. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher N-alkylpyrrolidones, e.g. N-octylpyrrolidone or N-cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite or others. The physical properties may be improved by addition of highly dispersed silica gel or polymers. Carriers for granules may be porous material, e.g. pumice, kaolin, sepiolite, bentonite; non-sorptive carriers may be calcite or sand or others. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the formulation or the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations which can be used according to the invention are:

| SC-I 1 | | |
|---|---|---|
| active ingredient | BP-1 | 100.0 g |
| Dispersing agent | Morwet D425[1] | 25.0 g |
| Dispersing agent | Pluronic ® PE10500[2] | 5.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxel ® GXL[4] | 1.0 g |
| Water | | to 1000 ml |
| SC-I 2 | | |
| active ingredient | BP-4 | 100.0 g |
| Dispersing agent | Soprophor ® FL[3] | 30.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxel ® GXL[4] | 1.0 g |
| Water | | to 1000 ml |
| SC-A-E | | |
| active ingredient | fungicide selected from classes (A) through (E) | 200.0 g |
| Dispersing agent | Soprophor ® FL[3] | 25.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxel ® GXL[4] | 1.0 g |
| Water | | to 1000 ml |

-continued

| SC-I + A-E | | |
|---|---|---|
| active ingredient | BP-4 | 60.0 g |
| active ingredient | fungicide selected from classes (A) through (E) | 120.0 g |
| Dispersing agent | Soprophor ® FL[3] | 25.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxel ® GXL[4] | 1.0 g |
| Water | | to 1000 ml |
| DC-I 1 | | |
| active ingredient | BP-4 | 100.0 g |
| Wetting agent | Pluronic ® PE6400[2] | 50.0 g |
| Dispersing agent | Lutensol ® TO 12[2] | 50.0 g |
| Solvent | benzyl alcohol | to 1000 ml |

[1] Product commercially available from Witco
[2] Product commercially available from BASF AG, Germany
[3] Product commercially available from Rhône-Poulenc
[4] Product commercially available from Zeneca The formulation SC-A–E comprising a compound selected from the classes (A) through (E) is in-tank mixed with any of the other formulations SC-I 1, SC-I 2, SC-I 3, or DC-I which comprise the compound of formula I.

In a preferred embodiment the active ingredients are added to the tank mix together each as solo formulation.

Therefore, the present invention relates to a kit for the preparation of a spray mixture consisting of two separate containments:
  (i) a containment which comprises at least one benzophenone of formula I, in particular one or more compounds selected from BP-1 through BP-4, conventional carriers and optionally adjuvants;
  (ii) a containment which comprises at least one active ingredient selected from the classes (A) through (E).

In a preferred embodiment the said kit will consist of two bottles with dispensing means which allow the easy and correct addition of the active ingredients (a) and (b) to the tank mix.

The formulation SC-I+A–E comprising BP-4 and a fungicidal active ingredient selected from the classes (A) through (E) as defined above can be used directly for preparing the tank mix according to the present invention.

A composition according to the invention preferably contains from 0.5% to 95% by weight of active ingredients.

As commodity the compositions may preferably be in a concentrated form whereas the end-user generally employs diluted compositions. The compositions may be diluted down to a concentration of 0.0001% of active ingredients.

The compositions of this invention can be applied to the plants or their environment simultaneous with or in succession with other active substances. These other active substances can be either fertilizers, agents which donate trace elements or other preparations which influence plant growth. However, they can also be other fungicides, selective herbicides, insecticides, bactericides, nematicides, algicides, molluscidides, rodenticides, virucides, compounds inducing resistance into plants, biological control agents such as viruses, bacteria, nematodes, fungi and other microorganisms, repellents of birds and animals, and plant growth regulators, or mixtures of several of these preparations, if appropriate together with other carrier substances conventionally used in the art of formulation, surfactants or other additives which promote application.

Examples of insecticidal compounds are alpha-cypermethrin, benfuracarb, BPMC, buprofezine, carbosulfan, cartap, chlorfenvinphos, chlorpyrifos-methyl, cycloprothrin, cypermethrin, esfenvalerate, ethofenprox, fenpropathrin, flucythrinate, flufenoxuron, hydramethyinon, imidacloprid, isoxathion, MEP, MPP, nitenpyram, PAP, permethrin, propaphos, pymetrozine, silafluofen, tebufenozide, teflubenzuron, temephos, terbufos, tetrachlorvinphos and triazamate.

Examples of biological control agents are: *Bacillus thuringiensis, Verticillium lecani, Autographica californica* NPV, *Beauvaria bassiana, Ampelomyces quisqualis, Bacilis subtilis, Pseudomonas cholororaphis, Pseudomonas fluorescens, Steptomyces griseoviridis* and *Trichoderma harzianum.*

Examples of chemical agents that induce systemic acquired resistance in plants such are: isonicotinic acid or derivatives thereof, 2,2-dichloro-3,3-dimethylcyclopropylcarboxylic acid.

The present invention is of wide applicability in the protection of crops, trees, residential and ornamental plants against fungal attack. Preferred crops are cereals, such as wheat and barley, rice as well as vines and apples. The duration of the protection is normally dependent on the individual compound selected, and also a variety of external factors, such as climate, whose impact is normally mitigated by the use of a suitable formulation.

The following examples further illustrate the present invention. It should be understood, however, that the invention is not limited solely to the particular examples given below.

EXAMPLES

General Methods

The trials are carried out under greenhouse (Examples 1 to 18) or field conditions (Example 19) in residual or curative applications. The fungicides are applied in single treatments, or in a combination comprising a benzophenone of formula I and a compound selected from the classes (A) through (E) as defined above. The compounds are applied in form of an aqueous spray mix obtained from concentrated formulation or the technical material.

I. Cereals and Dicots—Greenhouse

1. Seed is planted in 6 cm diameter plastic pots and maintained in the greenhouse.
  2. When the primary leaf is fully expanded in the case of cereals or several leaves are present in the case of dicots, formulated test compounds are sprayed with a three nozzle overhead fungicide sprayer to near run-off. Alternatively, a single nozzle overhead track sprayer is used for application of the compounds to cereals at a rate of 200 I/ha. Plants are then allowed to air-dry.
  3. Inoculation precedes treatment in the case of curative evaluations and follows treatment in case of residual evaluations. For inoculation of powdery mildew disease, plants are set up on greenhouse benches with bottom watering mats and inoculated by dusting them with conidia from infected plants. Between inoculation and treatment for curative evaluations and between treatment and inoculation for residual evaluations, plants are maintained in the greenhouse with bottom watering. For inoculation of non-powdery mildew diseases, an aqueous spore suspension of the pathogen is applied to the plant and the plants are kept 1–2 days in a moist infection chamber before being returned to the greenhouse where they are maintained by bottom watering.

4. Disease on the foliage as percent leaf area with disease symptoms/signs is evaluated about 7 days after inoculation. In the case of wheat, the tips and bases of the leaves are excluded from the evaluation.

$$\% \text{ disease control} = 100 - \frac{\% \text{ disease in treated plants}}{\% \text{ disease in untreated plants}} \times 100\%$$

Formulation, Reference Compounds and Controls

1. Technical compounds are formulated in a solvent/surfactant system consisting of 5% acetone and 0.05% Tween 20 in deionized water. Compounds are dissolved in acetone prior to addition of the water; the Tween 20 can be added through either the acetone or the water. Dilutions are made using the solvent/surfactant system. Formulated compounds are prepared using deionized water.
2. Two kinds of controls are included:
    Plants treated with the solvent/surfactant solution and inoculated (Solvent Blank).
    Untreated plants which are inoculated (Inoculated Control).

For the field study formulated benzophenones BP-1 through BP-4 and formulated compounds from the classes (A) through (E) were used.

Evaluation of the Disease

Assessments of the diseases took place at the indicated day after the application of the compounds. Per cent infected leaf area infected was evaluated. The efficacy of the compounds/compounds mixtures to control the diseases was calculated by using the formula given above under item 4:

II. Apple Fruit Botrytis

1. Apples (Malus X domestica Borkh.) variety "Golden Delicious" are disinfected by washing them briefly in 70% ethanol. After drying the apples are marked with four short equal-distant lines indicating the positions to be wounded.
2. Corresponding with the marks, four holes are poked around the apple equator with a pipette tip. 10 μl of the treatment solution are pipetted into each hole.
3. Three hours after application, 10 μl of a conidial suspension of Botrytis cinerea are pipetted into each hole. For incubation, the treated/inoculated apples are stored for five days.
4. Disease occurs as rotten apple tissue surrounding the inoculated wounds. The diameter of the rotten zone around each wound is measured.

Formulation, Reference Compounds and Controls

1. Technical compounds are formulated in a solvent system consisting of 5% acetone and 0.05% Tween 20 in deionized water. Compounds are dissolved in acetone prior to dilution with water. Formulated compounds are prepared using deionized water.
2. Three kinds of controls are included:
    Apples treated with the solvent solution and inoculated (Solvent Blank).
    Untreated apples which are inoculated (Inoculated Control).
    Untreated apples which are not inoculated (Uninoculated Control).

Evaluation of the Disease

Assessments of the diseases took place at the indicated day after the application of the compounds. Per cent infected leaf area infected was evaluated. The efficacy of the compounds/compounds mixtures to control the diseases was calculated by using the formula:

$$\% \text{ disease control} = 100 - \frac{\text{mean of diameters on treated apples}}{\text{mean of diameters on untreated apples}} \times 100\%$$

Determination of Synergy

Synergy was calculated using the % disease control values of specific treatments for the two COLBY formula given hereinabove III. Field Tests The compounds are applied according to good agricultural practice in form of an aqueous spray mix obtained from concentrated formulation or the technical material at a rate of 400 I/ha. The disease control is evaluated according to the formula given for the greenhouse tests.

A Greenhouse Tests

Example 1

Fungicidal Efficacy of the Mixture of BP-1+AP-1 (4 Day Curative) against *Erysiphe graminis* on Wheat The tank mix was obtained from technical materials of BP-1 and AP-1. The observed expected efficacies with different rates are given in Table I:

TABLE I

| dose rate (ppm) | | | |
| --- | --- | --- | --- |
| BP-1 | AP-1 | Observed Efficacy | Expected Efficacy |
| 125 | 0 | 42 | — |
| 25 | 0 | 1 | — |
| 0 | 125 | 0 | — |
| 0 | 25 | 0 | — |
| 125 | 125 | 56 | 42 |
| 125 | 25 | 54 | 42 |
| 25 | 125 | 21 | 1 |
| 25 | 25 | 4 | 1 |

Example 2

Fungicidal Efficacy of the Mixture of BP-1+AP-2 (4 Day Curative) against *Erysiphe graminis* on Wheat The tank mix was obtained from technical materials of BP-1 and AP-2. The observed and expected efficacies with different rates are given in Table II:

TABLE II

| dose rate (ppm) | | | |
| --- | --- | --- | --- |
| BP-1 | AP-2 | Observed Efficacy | Expected Efficacy |
| 125 | 0 | 42 | — |
| 25 | 0 | 1 | — |
| 0 | 125 | 8 | — |
| 0 | 25 | 0 | — |
| 125 | 125 | 67 | 47 |
| 125 | 25 | 73 | 42 |
| 25 | 125 | 20 | 9 |
| 25 | 25 | 9 | 1 |

Example 3

Fungicidal Efficacy of the Mixture of BP-1+ Triadimefon (4 Day Curative) against *Erysiphe graminis* on Wheat The tank mix was obtained from technical material of BP-1 and a wettable powder formulation containing 250 g/kg triadimefon. The observed and expected different rates are given in Table III:

TABLE III

| dose rate (ppm) | | Observed Efficacy | Expected Efficacy |
|---|---|---|---|
| BP-1 | triadimefon | | |
| 125 | 0 | 42 | — |
| 25 | 0 | 1 | — |
| 0 | 125 | 30 | — |
| 0 | 25 | 12 | — |
| 125 | 125 | 85 | 59 |
| 125 | 25 | 56 | 49 |
| 25 | 125 | 41 | 31 |
| 25 | 25 | 6 | 13 |

Example 4

**Fungicidal Efficacy of the Mixture of BP-5+ Triforine (3 Day Protective) against *Erysiphe graminis* on Wheat**

The tank mix was obtained from technical material of BP-5 and an EC formulation containing 190 g/l triforine. The observed and expected efficacies with different rates are given in Table IV:

TABLE IV

| dose rate (ppm) | | Observed Efficacy | Expected Efficacy |
|---|---|---|---|
| BP-5 | triforine | | |
| 25 | 0 | 31 | — |
| 5 | 0 | 12 | — |
| 0 | 125 | 12 | — |
| 25 | 125 | 59 | 41 |
| 5 | 25 | 26 | 24 |

Example 5

**Fungicidal Efficacy of the Mixture of BP-1+ Triadimefon (3 Day Protective) against *Erysiphe graminis* on Wheat**

The tank mix was obtained from technical material of BP-1 and a wettable powder formulation containing 250 g/kg triadimefon. The observed and expected efficacies with different rates are given in Table V:

TABLE V

| dose rate (ppm) | | Observed Efficacy | Expected Efficacy |
|---|---|---|---|
| BP-1 | triadimefon | | |
| 5 | 0 | 78 | — |
| 1 | 0 | 44 | — |
| 0 | 25 | 24 | — |
| 5 | 25 | 90 | 83 |
| 1 | 25 | 78 | 57 |

Example 6

**Fungicidal Efficacy of the Mixture of BP-4+Other Fungicides (4 Day Residual) against *Erysiphe cichoracearum* on Cucumbers**

The tank mixes were obtained technical material of BP-4 and different formulations of different active ingredients. The active ingredients, the type of formulations, the observed efficacies with different rates are given in table VI:

TABLE VI

| Compound | Formulation | dose rate (ppm) | Observed Efficacy | Expected Efficacy |
|---|---|---|---|---|
| BP-4 | TC 100% | 64 | 100 | |
| | | 16 | 51 | |
| | | 4 | 6 | |
| | | 1 | 1 | |
| Dithianon | WG 700 g/kg | 256 | 0 | |
| | | 64 | 0 | |
| | | 16 | 0 | |
| | | 4 | 0 | |
| Cyprodinil | TC 100% | 256 | 15 | |
| | | 64 | 0 | |
| | | 16 | 0 | |
| | | 4 | 0 | |
| Triforine | EC 190 g/l | 256 | 96 | |
| | | 64 | 79 | |
| | | 16 | 44 | |
| | | 4 | 1 | |
| Fenpropidin | EC 750 g/l | 256 | 69 | |
| | | 64 | 21 | |
| | | 16 | 6 | |
| | | 4 | 0 | |
| Mancozeb | WP 800 g/kg | 256 | 33 | |
| | | 64 | 1 | |
| | | 16 | 0 | |
| | | 4 | 0 | |
| Quinoxyfen | TC 100% | 256 | 100 | |
| | | 64 | 100 | |
| | | 16 | 100 | |
| | | 4 | 90 | |
| Chlorothalonil | SC 500 g/l | 256 | 1 | |
| | | 64 | 0 | |
| | | 16 | 0 | |
| | | 4 | 0 | |
| Ethirimol | SC 280 g/l | 256 | 100 | |
| | | 64 | 94 | |
| | | 16 | 83 | |
| | | 4 | 50 | |
| Dimethomorph | TC 100% | 256 | 18 | |
| | | 64 | 0 | |
| | | 16 | 0 | |
| | | 4 | 0 | |
| BION | WG 500 g/kg | 256 | 0 | |
| | | 64 | 0 | |
| | | 16 | 0 | |
| | | 4 | 0 | |
| Azoxystrobin | TC 100% | 256 | 100 | |
| | | 64 | 100 | |
| | | 16 | 96 | |
| | | 4 | 78 | |
| BP-4 + Dithianon | Tankmix | 64 + 256 | 100 | 100 |
| | | 16 + 64 | 73 | 51 |
| | | 4 + 16 | 31 | 6 |
| | | 1 + 4 | 29 | 1 |
| BP-4 + Cyprodinil | Tankmix | 64 + 256 | 92 | 100 |
| | | 16 + 64 | 59 | 51 |
| | | 4 + 16 | 51 | 6 |
| | | 1 + 4 | 32 | 1 |
| BP-4 + Triforine | Tankmix | 64 + 256 | 100 | 100 |
| | | 16 + 64 | 99 | 90 |
| | | 4 + 16 | 65 | 47 |
| | | 1 + 4 | 31 | 3 |
| BP-4 + Fenpropidin | Tankmix | 64 + 256 | 100 | 100 |
| | | 16 + 64 | 96 | 61 |
| | | 4 + 16 | 60 | 12 |
| | | 1 + 4 | 56 | 1 |
| BP-4 + Mancozeb | Tankmix | 64 + 256 | 100 | 100 |
| | | 16 + 64 | 99 | 52 |
| | | 4 + 16 | 54 | 6 |
| | | 1 + 4 | 38 | 1 |
| BP-4 + Quinoxyfen | Tankmix | 64 + 256 | 100 | 100 |
| | | 16 + 64 | 100 | 100 |
| | | 4 + 16 | 100 | 100 |
| | | 1 + 4 | 100 | 91 |

TABLE VI-continued

| Compound | Formulation | dose rate (ppm) | Observed Efficacy | Expected Efficacy |
|---|---|---|---|---|
| BP-4 + Chlorothalonil | Tankmix | 64 + 256 | 100 | 100 |
| | | 16 + 64 | 99 | 51 |
| | | 4 + 16 | 22 | 6 |
| | | 1 + 4 | 14 | 1 |
| BP-4 + Ethirimol | Tankmix | 64 + 256 | 100 | 100 |
| | | 16 + 64 | 100 | 97 |
| | | 4 + 16 | 85 | 84 |
| | | 1 + 4 | 53 | 51 |
| BP-4 + Dimethomorph | Tankmix | 64 + 256 | 100 | 100 |
| | | 16 + 64 | 99 | 51 |
| | | 4 + 16 | 37 | 6 |
| | | 1 + 4 | 10 | 1 |
| BP-4 + BION | Tankmix | 64 + 256 | 100 | 100 |
| | | 16 + 64 | 53 | 51 |
| | | 4 + 16 | 12 | 6 |
| | | 1 + 4 | 1 | 1 |
| BP-4 + Azoxystrobin | Tankmix | 64 + 256 | 100 | 100 |
| | | 16 + 64 | 100 | 100 |
| | | 4 + 16 | 99 | 96 |
| | | 1 + 4 | 92 | 78 |

Example 7

Fungicidal Efficacy of the Mixture of BP-4+Other Fungicides (4 Day Residual) against *Puccinia recondita* on Wheat The tank mixes were obtained from technical material of BP-4 and different formulations of different active ingredients. The active ingredients, the type of formulations, the observed and expected efficacies with different rates are given in Table VII:

TABLE VII

| Compound | Formulation | dose rate (ppm) | Observed Efficacy | Expected Efficacy |
|---|---|---|---|---|
| BP-4 | TC 100% | 256 | 13 | |
| | | 64 | 0 | |
| | | 16 | 0 | |
| | | 4 | 0 | |
| Dithianon | WG 700 g/kg | 256 | 95 | |
| | | 64 | 84 | |
| | | 16 | 16 | |
| | | 4 | 4 | |
| Cyprodinil | TC 100 % | 256 | 0 | |
| | | 64 | 0 | |
| | | 16 | 0 | |
| | | 4 | 0 | |
| Triforine | EC 190 g/l | 256 | 100 | |
| | | 64 | 90 | |
| | | 16 | 7 | |
| | | 4 | 0 | |
| Fenpropidin | EC 750 g/l | 256 | 97 | |
| | | 64 | 8 | |
| | | 16 | 0 | |
| | | 4 | 0 | |
| Mancozeb | WP 800 g/kg | 256 | 91 | |
| | | 64 | 28 | |
| | | 16 | 0 | |
| | | 4 | 0 | |
| Quinoxyfen | TC 100% | 256 | 0 | |
| | | 64 | 0 | |
| | | 16 | 0 | |
| | | 4 | 0 | |
| Chlorothalonil | SC 500 g/l | 256 | 31 | |
| | | 64 | 0 | |
| | | 16 | 0 | |
| | | 4 | 0 | |

TABLE VII-continued

| Compound | Formulation | dose rate (ppm) | Observed Efficacy | Expected Efficacy |
|---|---|---|---|---|
| Ethirimol | SC 280 g/l | 256 | 0 | |
| | | 64 | 0 | |
| | | 16 | 0 | |
| Dimethomorph | TC 100 % | 256 | 0 | |
| | | 64 | 0 | |
| | | 16 | 0 | |
| BION | WG 500 g/kg | 256 | 0 | |
| | | 64 | 0 | |
| | | 16 | 0 | |
| | | 4 | 0 | |
| BP-4 + Dithianon | Tankmix | 256 + 256 | 100 | 95 |
| | | 64 + 64 | 100 | 84 |
| | | 16 + 16 | 100 | 16 |
| | | 4 + 4 | 100 | 4 |
| BP-4 + Cyprodinil | Tankmix | 256 + 256 | 100 | 13 |
| | | 64 + 64 | 100 | 0 |
| | | 16 + 16 | 100 | 0 |
| | | 4 + 4 | 100 | 0 |
| BP-4 + Triforine | Tankmix | 256 + 256 | 100 | 100 |
| | | 64 + 64 | 100 | 90 |
| | | 16 + 16 | 100 | 7 |
| | | 4 + 4 | 100 | 0 |
| BP-4 + Fenpropidin | Tankmix | 256 + 256 | 100 | 97 |
| | | 64 + 64 | 96 | 8 |
| | | 16 + 16 | 93 | 0 |
| | | 4 + 4 | 91 | 0 |
| BP-4 + Mancozeb | Tankmix | 256 + 256 | 100 | 92 |
| | | 64 + 64 | 97 | 28 |
| | | 16 + 16 | 94 | 0 |
| | | 4 + 4 | 92 | 0 |
| BP-4 + Quinoxyfen | Tankmix | 256 + 256 | 89 | 13 |
| | | 64 + 64 | 96 | 0 |
| | | 16 + 16 | 95 | 0 |
| | | 4 + 4 | 93 | 0 |
| BP-4 + Chlorothalonil | Tankmix | 256 + 256 | 100 | 40 |
| | | 64 + 64 | 36 | 0 |
| | | 16 + 16 | 40 | 0 |
| | | 4 + 4 | 9 | 0 |
| BP-4 + Ethirimol | Tankmix | 256 + 256 | 96 | 13 |
| | | 64 + 64 | 96 | 0 |
| | | 16 + 16 | 64 | 0 |
| BP-4 + Dimethomorph | Tankmix | 256 + 256 | 54 | 13 |
| | | 64 + 64 | 28 | 0 |
| | | 16 + 16 | 6 | 0 |
| BP-4 + BION | Tankmix | 256 + 256 | 75 | 13 |
| | | 64 + 64 | 78 | 0 |
| | | 16 + 16 | 64 | 0 |
| | | 4 + 4 | 59 | 0 |

Example 8

Fungicidal Efficacy of the Mixture of BP-4+Other Fungicides (4 Day Residual) against *Leptosphaeria nodorum* on Wheat The tank mixes were obtained from technical material of BP-4 and different formulations of different active ingredients. The active ingredients, the type of formulations, the observed and expected efficacies with different rates are given in Table VIII:

TABLE VIII

| Compound | Formulation | dose rate (ppm) | Observed Efficacy | Expected Efficacy |
|---|---|---|---|---|
| BP-4 | TC 100% | 256 | 34 | |
| | | 64 | 14 | |
| | | 16 | 0 | |
| | | 4 | 0 | |

TABLE VIII-continued

| Compound | Formulation | dose rate (ppm) | Observed Efficacy | Expected Efficacy |
|---|---|---|---|---|
| Dithianon | WG 700 g/kg | 256 | 74 | |
| | | 64 | 37 | |
| | | 16 | 1 | |
| | | 4 | 0 | |
| Cyprodinil | TC 100 % | 256 | 93 | |
| | | 64 | 88 | |
| | | 16 | 75 | |
| | | 4 | 0 | |
| Tritorine | EC 190 g/l | 256 | 85 | |
| | | 64 | 51 | |
| | | 16 | 31 | |
| | | 4 | 4 | |
| | | 1 | 0 | |
| Fenpropidin | EC 750 g/l | 256 | 21 | |
| | | 64 | 0 | |
| Mancozeb | WP 800 g/kg | 256 | 69 | |
| | | 64 | 47 | |
| | | 16 | 21 | |
| | | 4 | 0 | |
| Quinoxyfen | TC 100% | 256 | 18 | |
| | | 64 | 0 | |
| | | 16 | 1 | |
| Dimethomorph | TC 100% | 256 | 14 | |
| | | 64 | 11 | |
| | | 16 | 6 | |
| | | 4 | 1 | |
| Azoxystrobin | TC 100% | 256 | 100 | |
| | | 64 | 100 | |
| | | 16 | 97 | |
| | | 4 | 84 | |
| BP-4 + Dithianon | Tankmix | 256 + 256 | 90 | 83 |
| | | 64 + 64 | 65 | 46 |
| | | 16 + 16 | 27 | 1 |
| | | 4 + 4 | 4 | 0 |
| BP-4 + Cyprodinil | Tankmix | 256 + 256 | 97 | 96 |
| | | 64 + 64 | 92 | 90 |
| | | 16 + 16 | 80 | 75 |
| | | 4 + 4 | 57 | 0 |
| BP-4 + Triforine | Tankmix | 256 + 256 | 97 | 90 |
| | | 64 + 64 | 84 | 58 |
| | | 16 + 16 | 47 | 31 |
| | | 4 + 4 | 32 | 4 |
| BP-4 + Fenpropidin | Tankmix | 256 + 256 | 42 | 48 |
| | | 64 + 64 | 21 | 14 |
| BP-4 + Mancozeb | Tankmix | 256 + 256 | 87 | 79 |
| | | 64 + 64 | 65 | 55 |
| | | 16 + 16 | 32 | 21 |
| | | 4 + 4 | 8 | 0 |
| BP-4 + Quinoxyfen | Tankmix | 256 + 256 | 62 | 46 |
| | | 64 + 64 | 34 | 14 |
| | | 16 + 16 | 8 | 1 |
| BP-4 + CL 336 370 Dimethomorph | Tankmix | 256 + 256 | 84 | 43 |
| | | 64 + 64 | 65 | 24 |
| | | 16 + 16 | 31 | 6 |
| | | 4 + 4 | 14 | 1 |
| BP4+ Azoxystrobin | Tankmix | 256 + 256 | 100 | 100 |
| | | 64 + 64 | 100 | 100 |
| | | 16 + 16 | 98 | 97 |
| | | 4 + 4 | 95 | 84 |

Example 9

Fungicidal Efficacy of the Mixture of BP-4+Other Fungicides (4 Day Residual) against *Puccinia recondita* on Wheat The tank mixes were obtained from technical material of BP-4 and different formulations of different active ingredients. The active ingredients, the type of formulations, the observed and expected efficacies with different rates are given in Table IX:

TABLE IX

| Compound | Formulation | dose rate (ppm) | Observed Efficacy | Expected Efficacy |
|---|---|---|---|---|
| BP-4 | TC 100% | 256 | 38 | |
| | | 64 | 16 | |
| | | 16 | 4 | |
| | | 4 | 6 | |
| Captan | WP 500 g/kg | 256 | 89 | |
| | | 64 | 55 | |
| | | 16 | 11 | |
| | | 4 | 4 | |
| Fluazinam | SC 500 g/l | 256 | 80 | |
| | | 64 | 22 | |
| | | 16 | 6 | |
| | | 4 | 0 | |
| Metalaxyl | TC 100% | 256 | 12 | |
| | | 64 | 0 | |
| Fenpiclonil | TC 100% | 256 | 58 | |
| | | 64 | 18 | |
| | | 16 | 0 | |
| | | 4 | 1 | |
| Famoxadone | TC 100% | 64 | 92 | |
| | | 16 | 80 | |
| | | 4 | 45 | |
| BP-4 + Captan | Tankmix | 256 + 256 | 95 | 93 |
| | | 64 + 64 | 65 | 62 |
| | | 16 + 16 | 30 | 15 |
| BP-4 + Fluazinam | Tankmix | 256 + 256 | 97 | 88 |
| | | 64 + 64 | 53 | 35 |
| | | 16 + 16 | 20 | 10 |
| BP-4 + Metalaxyl | Tankmix | 256 + 256 | 61 | 46 |
| | | 64 + 64 | 19 | 16 |
| BP-4 + Fenpiclonil | Tankmix | 256 + 256 | 81 | 74 |
| | | 64 + 64 | 54 | 31 |
| | | 16 + 16 | 12 | 4 |
| | | 4 + 4 | 7 | 7 |
| BP-4 + Famoxadone | Tankmix | 64 + 64 | 93 | 93 |
| | | 16 + 16 | 83 | 81 |
| | | 4 + 4 | 60 | 48 |

Example 10

Fungicidal Efficacy of the Mixture BP-4+Other Fungicides (4 Day Residual) against *Leptosphaeria nodorum* on Wheat The tank mixes were obtained from material of BP-4 and different formulations of different active ingredients. The active ingredients, the type of formulations, the observed and expected efficacies with different rates are given in Table X:

TABLE X

| Compound | Formulation | dose rate (ppm) | Observed Efficacy | Expected Efficacy |
|---|---|---|---|---|
| BP-4 | TC 100% | 256 | 44 | |
| | | 64 | 18 | |
| | | 16 | 10 | |
| | | 4 | 0 | |
| Dodine | WP 650 g/kg | 256 | 59 | |
| | | 64 | 24 | |
| | | 16 | 6 | |
| | | 4 | 0 | |
| Captan | WP 500 g/kg | 256 | 90 | |
| | | 64 | 84 | |
| Fluazinam | SC 500 g/l | 256 | 91 | |
| | | 64 | 81 | |
| Famoxadone | TC 100% | 256 | 97 | |
| | | 64 | 80 | |
| | | 16 | 69 | |
| | | 4 | 66 | |

TABLE X-continued

| Compound | Formulation | dose rate (ppm) | Observed Efficacy | Expected Efficacy |
|---|---|---|---|---|
| BP-4 + Dodine | Tankmix | 256 + 256 | 75 | 77 |
| | | 64 + 64 | 57 | 38 |
| | | 16 + 16 | 29 | 15 |
| | | 4 + 4 | 10 | 0 |
| BP-4+ Captan | Tankmix | 256 + 256 | 96 | 94 |
| | | 64 + 64 | 93 | 87 |
| BP-4 + Fluazinam | Tankmix | 256 + 256 | 95 | 95 |
| | | 64 + 64 | 91 | 84 |
| BP-4 + Famoxadone | Tankmix | 256 + 256 | 94 | 98 |
| | | 64 + 64 | 89 | 84 |
| | | 16 + 16 | 86 | 72 |
| | | 4 + 4 | 67 | 66 |

Example 11

Fungicidal Efficacy of the Mixture of BP-4+Other Fungicides (4 Day Residual) against *Erysiphe cichoracearum* on Cucumbers The tank mixes were obtained from technical material of BP-4 and different formulations of different active ingredients. The active ingredients, the type of formulations, the observed and expected efficacies with different rates are given in Table XI:

TABLE XI

| Compound | Formulation | dose rate (ppm) | Observed Efficacy | Expected Efficacy |
|---|---|---|---|---|
| BP-4 | TC 100% | 50 | 96 | |
| | | 10 | 55 | |
| | | 2 | 2 | |
| | | 0.4 | 0 | |
| Sulfur inorganic | TC 100% | 50 | 0 | |
| | | 10 | 7 | |
| | | 2 | 0 | |
| | | 0.4 | 0 | |
| Propiconazole | EC 250 g/l | 50 | 96 | |
| | | 10 | 76 | |
| | | 2 | 19 | |
| | | 0.4 | 0 | |
| Epoxiconazole | SC 125 g/l | 50 | 77 | |
| | | 10 | 68 | |
| | | 2 | 46 | |
| | | 0.4 | 0 | |
| Tebuconazole | EC 250 g/l | 50 | 95 | |
| | | 10 | 79 | |
| | | 2 | 45 | |
| | | 0.4 | 10 | |
| Metconazole | SL 60 g/l | 50 | 99 | |
| | | 10 | 75 | |
| | | 0.4 | 2 | |
| Myclobutanil | WP 60 g/kg | 50 | 96 | |
| | | 10 | 73 | |
| | | 2 | 52 | |
| | | 0.4 | 36 | |
| Kresoxim-methyl | WG 500 g/kg | 50 | 100 | |
| | | 10 | 88 | |
| | | 2 | 14 | |
| | | 0.4 | 2 | |
| AC 382042 | TC 100% | 50 | 25 | |
| | | 10 | 14 | |
| | | 2 | 3 | |
| | | 0.4 | 7 | |
| BRIO Epoxiconazole (150 g/l)/ | SE 450 g/l /Fenproplmorph (300 g/l) | 50 | 96 | |
| | | 10 | 48 | |
| ACROBAT MZ Dimethomorph (90 g/kg) | WP 690 g/kg /Mancozeb /(600 g/kg) | 50 | 57 | |
| | | 10 | 30 | |
| | | 2 | 0 | |
| | | 0.4 | 0 | |

TABLE XI-continued

| Compound | Formulation | dose rate (ppm) | Observed Efficacy | Expected Efficacy |
|---|---|---|---|---|
| JUWEL Kresoxim-methyl (125 g/l) | SC 250 g/l /Epoxiconazole. /(125 g/l) | 50 | 100 | |
| | | 10 | 98 | |
| | | 2 | 71 | |
| | | 0.4 | 37 | |
| BP-4 Sulfur inorganic | Tankmix | 50 + 50 | 92 | 96 |
| | | 10 + 10 | 70 | 58 |
| | | 2 + 2 | 10 | 2 |
| | | 0.4 + 0.4 | 9 | 0 |
| BP-4 Propiconazole | Tankmix | 50 + 50 | 100 | 100 |
| | | 10 + 10 | 100 | 89 |
| | | 2 + 2 | 61 | 21 |
| | | 0.4 + 0.4 | 28 | 0 |
| BP-4 Epoxiconazole | Tankmix | 50 + 50 | 100 | 99 |
| | | 10 + 10 | 98 | 86 |
| | | 2 + 2 | 71 | 47 |
| | | 0.4 + 0.4 | 41 | 0 |
| BP-4 Tebuconazole | Tankmix | 50 + 50 | 100 | 100 |
| | | 10 + 10 | 98 | 91 |
| | | 2 + 2 | 48 | 45 |
| | | 0.4 + 0.4 | 28 | 10 |
| BP-4 Metconazole | Tankmix | 50 + 50 | 100 | 100 |
| | | 10 + 10 | 97 | 89 |
| | | 0.4 + 0.4 | 5 | 2 |
| BP-4 Myclobutanil | Tankmix | 50 + 50 | 100 | 100 |
| | | 10 + 10 | 99 | 88 |
| | | 2 + 2 | 75 | 52 |
| | | 0.4 + 0.4 | 55 | 36 |
| BP-4 Kresoxim-methyl | Tankmix | 50 + 50 | 100 | 100 |
| | | 10 + 10 | 100 | 95 |
| | | 2 + 2 | 37 | 15 |
| | | 0.4 + 0.4 | 2 | 2 |
| BP-4 AC 382042 | Tankmix | 50 + 50 | 100 | 97 |
| | | 10 + 10 | 87 | 62 |
| | | 2 + 2 | 28 | 5 |
| | | 0.4 + 0.4 | 25 | 7 |
| BP-4 BRIO | Tankmix | 50 + 50 | 100 | 100 |
| | | 10 + 10 | 85 | 77 |
| BP-4 ACROBAT MZ | Tankmix | 50 + 50 | 100 | 98 |
| | | 10 + 10 | 89 | 69 |
| | | 2 + 2 | 45 | 2 |
| | | 0.4 + 0.4 | 7 | 0 |
| BP-4 JUWEL | Tankmix | 50 + 50 | 100 | 100 |
| | | 10 + 10 | 98 | 99 |
| | | 2 + 2 | 84 | 72 |
| | | 0.4 + 0.4 | 50 | 37 |

Example 12

Fungicidal Efficacy of the Mixture of BP-4+ Myclobutanil (4 Day Residual) against *Puccinia recondita* on Wheat The tank mixes were obtained from technical material of BP-4 and Myclobutanil. The type of formulation, the observed and expected efficacies with different rates are given in Table XII:

TABLE XII

| Compound | Formulation | dose rate (ppm) | Observed Efficacy | Expected Efficacy |
|---|---|---|---|---|
| BP-4 | TC 100% | 50 | 31 | |
| | | 10 | 10 | |
| | | 2 | 7 | |
| | | 0.4 | 2 | |
| Myclobutanil | WP 60 g/kg | 50 | 99 | |
| | | 10 | 72 | |
| | | 2 | 52 | |
| | | 0.4 | 13 | |

TABLE XII-continued

| Compound | Formulation | dose rate (ppm) | Observed Efficacy | Expected Efficacy |
|---|---|---|---|---|
| BP-4 Myclobutanil | Tankmix | 50 + 50 | 99 | 99 |
| | | 10 + 10 | 86 | 75 |
| | | 2 + 2 | 65 | 55 |
| | | 0.4 + 0.4 | 48 | 14 |

Example 13

Fungicidal Efficacy of the Mixture of BP-4+Other Fungicides (4 Day Residual) against *Pyrenophora teres* on Barley The tank mixes were obtained from technical material of BP-4 and different formulations of different active ingredients. The active ingredients, the type of formulations, the observed and expected efficacies with different rates are given in Table XIII:

TABLE XIII

| Compound | Formulation | dose rate (ppm) | Observed Efficacy | Expected Efficacy |
|---|---|---|---|---|
| BP-4 | TC 100% | 50 | 58 | |
| | | 10 | 34 | |
| | | 2 | 0 | |
| | | 0.4 | 0 | |
| Sulfur inorganic | TC 100% | 10 | 0 | |
| | | 2 | 0 | |
| Copper oxychloride | WP 450 g/kg | 50 | 14 | |
| | | 10 | 14 | |
| | | 2 | 0 | |
| | | 0.4 | 0 | |
| Propiconazole | EC 250 g/l | 50 | 74 | |
| | | 10 | 38 | |
| | | 2 | 0 | |
| | | 0.4 | 0 | |
| Metconazole | SL 60 g/l | 10 | 47 | |
| | | 0.4 | 0 | |
| Myclobutanil | WP 60 g/kg | 50 | 82 | |
| | | 10 | 40 | |
| | | 2 | 21 | |
| | | 0.4 | 0 | |
| Kresoxim-methyl | WG 500 g/kg | 2 | 21 | |
| | | 0.4 | 0 | |
| ACROBAT MZ Dimethomorph/ Mancozeb | WP 690 g/kg | 50 | 47 | |
| | | 10 | 23 | |
| | | 2 | 12 | |
| | | 0.4 | 0 | |
| JUWEL kresoxim-methyl/ Epoxiconazole | SC 250 g/l | 50 | 89 | |
| | | 10 | 62 | |
| | | 2 | 45 | |
| | | 0.4 | 5 | |
| BP-4 Sulfur inorganic | Tankmix | 10 + 10 | 49 | 34 |
| | | 2 + 2 | 0 | 0 |
| BP-4 Copper oxychloride | Tankmix | 50 + 50 | 78 | 64 |
| | | 10 + 10 | 54 | 43 |
| | | 2 + 2 | 38 | 0 |
| | | 0.4 + 0.4 | 0 | 0 |
| BP-4 Propiconazole | Tankmix | 50 + 50 | 89 | 89 |
| | | 10 + 10 | 78 | 59 |
| | | 2 + 2 | 32 | 0 |
| | | 0.4 + 0.4 | 0 | 0 |
| BP-4 Tebuconazole | Tankmix | 50 + 50 | 89 | 86 |
| | | 2 + 2 | 14 | 5 |
| | | 0.4 + 0.4 | 0 | 0 |
| BP-4 Metconazole | Tankmix | 10 + 10 | 69 | 65 |
| | | 2 + 2 | 25 | 32 |
| | | 0.4 + 0.4 | 18 | 0 |

TABLE XIII-continued

| Compound | Formulation | dose rate (ppm) | Observed Efficacy | Expected Efficacy |
|---|---|---|---|---|
| BP-4 Myclobutanil | Tankmix | 50 + 50 | 91 | 93 |
| | | 10 + 10 | 67 | 61 |
| | | 2 + 2 | 40 | 21 |
| | | 0.4 + 0.4 | 7 | 0 |
| BP-4 Kresoxim-methyl | Tankmix | 2 + 2 | 67 | 21 |
| | | 0.4 + 0.4 | 36 | 0 |
| BP-4 ACROBAT MZ | Tankmix | 50 + 50 | 85 | 78 |
| | | 10 + 10 | 60 | 49 |
| | | 2 + 2 | 29 | 12 |
| | | 0.4 + 0.4 | 0 | 0 |
| BP-4 JUWEL | Tankmix | 50 + 50 | 100 | 95 |
| | | 10 + 10 | 78 | 75 |
| | | 2 + 2 | 49 | 45 |
| | | 0.4 + 0.4 | 40 | 5 |

Example 14

Fungicidal Efficacy of the Mixture of BP-4+Other Fungicides (4 Day Residual) against *Erysiphe cichoracearum* on Cucumbers The tank mixes were obtained from technical material of BP-4 and different formulations of different active ingredients. The active ingredients, the type of formulations, the observed and expected efficacies with different rates are given in Table XIV:

TABLE XIV

| Compound | Formulation | dose rate (ppm) | Observed Efficacy | Expected Efficacy |
|---|---|---|---|---|
| BP-4 | TC 100% | 50 | 97 | |
| | | 10 | 13 | |
| | | 2 | 0 | |
| | | 0.4 | 0 | |
| Cyproconazole | SL 100 g/l | 10 | 68 | |
| | | 0.4 | 19 | |
| Dinocap | WP 190 g/kg | 10 | 0 | |
| | | 2 | 0 | |
| | | 0.4 | 0 | |
| Fenarimol | SC 125 g/l | 50 | 67 | |
| | | 10 | 42 | |
| | | 2 | 34 | |
| | | 0.4 | 5 | |
| Fenpropimorph | EC 750 g/l | 10 | 7 | |
| | | 2 | 0 | |
| | | 0.4 | 0 | |
| Flusilazole | WP 200 g/kg | 50 | 38 | |
| | | 10 | 19 | |
| | | 2 | 0 | |
| | | 0.4 | 0 | |
| Penconazole | EC 100 g/l | 50 | 67 | |
| | | 10 | 37 | |
| | | 2 | 35 | |
| | | 0.4 | 6 | |
| Prochloraz | EC 400 g/l | 50 | 18 | |
| | | 10 | 1 | |
| | | 2 | 0 | |
| | | 0.4 | 0 | |
| Pyrifenox | WP 500 g/kg | 50 | 20 | |
| | | 10 | 1 | |
| | | 2 | 0 | |
| | | 0.4 | 0 | |
| Triadimefon | WP 250 g/kg | 50 | 47 | |
| | | 10 | 23 | |
| | | 2 | 6 | |
| | | 0.4 | 0 | |

TABLE XIV-continued

| Compound | Formulation | dose rate (ppm) | Observed Efficacy | Expected Efficacy |
|---|---|---|---|---|
| Triadimenol | EC 250 g/l | 50 | 68 | |
| | | 10 | 45 | |
| | | 2 | 21 | |
| | | 0.4 | 1 | |
| Spiroxamine | EC 500 g/l | 10 | 2 | |
| | | 2 | 0 | |
| | | 0.4 | 0 | |
| BP-4 Cyproconazole | Tankmix | 10 + 10 | 84 | 72 |
| | | 0.4 + 0.4 | 23 | 19 |
| BP-4 Dinocap | Tankmix | 50 + 50 | 96 | 98 |
| | | 10 + 10 | 30 | 13 |
| | | 2 + 2 | 2 | 0 |
| | | 0.4 + 0.4 | 2 | 0 |
| BP-4 Fenarimol | Tankmix | 50 + 50 | 100 | 99 |
| | | 10 + 10 | 92 | 49 |
| | | 2 + 2 | 49 | 34 |
| | | 0.4 + 0.4 | 19 | 5 |
| BP-4 Fenpropimorph | Tankmix | 10 + 10 | 43 | 19 |
| | | 2 + 2 | 6 | 0 |
| | | 0.4 + 0.4 | 2 | 0 |
| BP-4 Flusilazole | Tankmix | 50 + 50 | 100 | 98 |
| | | 10 + 10 | 57 | 29 |
| | | 2 + 2 | 14 | 0 |
| | | 0.4 + 0.4 | 1 | 0 |
| BP-4 Penconazole | Tankmix | 50 + 50 | 100 | 99 |
| | | 10 + 10 | 96 | 45 |
| | | 2 + 2 | 66 | 35 |
| | | 0.4 + 0.4 | 23 | 6 |
| BP-4 Prochloraz | Tankmix | 50 + 50 | 100 | 98 |
| | | 10 + 10 | 71 | 13 |
| | | 2 + 2 | 11 | 0 |
| | | 0.4 + 0.4 | 7 | 0 |
| BP-4 Pyrifenox | Tankmix | 50 + 50 | 100 | 98 |
| | | 10 + 10 | 56 | 13 |
| | | 2 + 2 | 7 | 0 |
| | | 0.4 + 0.4 | 4 | 0 |
| BP-4 Triadimefon | Tankmix | 50 + 50 | 99 | 99 |
| | | 10 + 10 | 39 | 32 |
| | | 2 + 2 | 15 | 6 |
| | | 0.4 + 0.4 | 2 | 0 |
| BP-4 Triadimenol | Tankmix | 50 + 50 | 100 | 99 |
| | | 10 + 10 | 78 | 52 |
| | | 2 + 2 | 30 | 21 |
| | | 0.4 + 0.4 | 9 | 1 |
| BP-4 Spiroxamine | Tankmix | 10 + 10 | 37 | 15 |
| | | 2 + 2 | 10 | 0 |
| | | 0.4 + 0.4 | 2 | 0 |

Example 15

Fungicidal Efficacy of the Mixture of BP-4+Other Fungicides (4 Day Residual) against *Puccinia recondita* on Wheat The tank mixes were obtained from technical material of BP-4 and different formulations of different active ingredients. The active ingredients, the type of formulations, the observed and expected efficacies with different rates are given in Table XV:

TABLE XV

| Compound | Formulation | dose rate (ppm) | Observed Efficacy | Expected Efficacy |
|---|---|---|---|---|
| BP-4 | TC 100% | 50 | 12 | |
| | | 10 | 6 | |
| | | 2 | 0 | |
| | | 0.4 | 0 | |
| Cyproconazole | SL 100 g/l | 2 | 99 | |
| | | 0.4 | 88 | |

TABLE XV-continued

| Compound | Formulation | dose rate (ppm) | Observed Efficacy | Expected Efficacy |
|---|---|---|---|---|
| Dinocap | WP 190 g/kg | 50 | 54 | |
| | | 10 | 23 | |
| | | 2 | 13 | |
| | | 0.4 | 4 | |
| Fenarimol | SC 125 g/l | 50 | 90 | |
| | | 10 | 23 | |
| | | 2 | 9 | |
| | | 0.4 | 0 | |
| Fenpropimorph | EC 750 g/l | 50 | 60 | |
| | | 2 | 15 | |
| | | 0.4 | 2 | |
| Flusilazole | WP 200 g/kg | 50 | 100 | |
| | | 2 | 28 | |
| | | 0.4 | 5 | |
| Penconazole | EC 100 g/l | 50 | 26 | |
| | | 10 | 10 | |
| | | 2 | 3 | |
| | | 0.4 | 0 | |
| Prochloraz | EC 400 g/l | 50 | 14 | |
| | | 10 | 1 | |
| | | 2 | 0 | |
| | | 0.4 | 0 | |
| Pyrifenox | WP 500 g/kg | 50 | 6 | |
| | | 10 | 1 | |
| | | 2 | 0 | |
| | | 0.4 | 0 | |
| Triadimenol | EC 250 g/l | 50 | 98 | |
| | | 10 | 69 | |
| | | 2 | 21 | |
| | | 0.4 | 1 | |
| Spiroxamine | EC 500 g/l | 50 | 17 | |
| | | 10 | 4 | |
| | | 2 | 0 | |
| BP-4 Cyproconazole | Tankmix | 2 + 2 | 100 | 99 |
| | | 0.4 + 0.4 | 92 | 88 |
| BP-4 Dinocap | Tankmix | 50 + 50 | 61 | 60 |
| | | 10 + 10 | 38 | 28 |
| | | 2 + 2 | 26 | 13 |
| | | 0.4 + 0.4 | 10 | 4 |
| BP-4 Fenarimol | Tankmix | 50 + 50 | 99 | 91 |
| | | 10 + 10 | 52 | 28 |
| | | 2 + 2 | 15 | 9 |
| | | 0.4 + 0.4 | 12 | 0 |
| BP-4 Fenpropimorph | Tankmix | 50 + 50 | 84 | 65 |
| | | 2 + 2 | 19 | 15 |
| | | 0.4 + 0.4 | 13 | 2 |
| BP-4 Flusilazole | Tankmix | 50 + 50 | 100 | 100 |
| | | 2 + 2 | 55 | 28 |
| | | 0.4 + 0.4 | 14 | 5 |
| BP-4 Penconazole | Tankmix | 50 + 50 | 78 | 35 |
| | | 10 + 10 | 19 | 16 |
| | | 2 + 2 | 7 | 3 |
| | | 0.4 + 0.4 | 4 | 0 |
| BP-4 Prochloraz | Tankmix | 50 + 50 | 34 | 25 |
| | | 10 + 10 | 12 | 7 |
| | | 2 + 2 | 4 | 0 |
| | | 0.4 + 0.4 | 0 | 0 |
| BP-4 Pyrifenox | Tankmix | 50 + 50 | 31 | 18 |
| | | 10 + 10 | 15 | 7 |
| | | 2 + 2 | 5 | 0 |
| | | 0.4 + 0.4 | 4 | 0 |
| BP-4 Triadimenol | Tankmix | 50 + 50 | 98 | 98 |
| | | 10 + 10 | 89 | 71 |
| | | 2 + 2 | 39 | 21 |
| | | 0.4 + 0.4 | 10 | 1 |
| BP-4 Spiroxamine | Tankmix | 50 + 50 | 40 | 27 |
| | | 10 + 10 | 11 | 10 |
| | | 2 + 2 | 3 | 0 |

Example 16

Fungicidal Efficacy of the Mixture of BP-4+Other Fungicides (4 Day Residual) against *Pyrenophora teres* on Barley The tank mixes were obtained from technical material of BP-4 and different formulations of different active ingredients. The active ingredients, the type of formulations, the observed and expected efficacies with different rates are given in Table XVI:

TABLE XVI

| Compound | Formulation | dose rate (ppm) | Observed Efficacy | Expected Efficacy |
|---|---|---|---|---|
| BP-4 | TC 100% | 50 | 11 | |
| | | 10 | 0 | |
| | | 2 | 0 | |
| | | 0.4 | 0 | |
| Cyproconazole | SL 100 g/l | 10 | 1 | |
| | | 2 | 4 | |
| Dinocap | WP 190 g/kg | 50 | 22 | |
| | | 10 | 5 | |
| | | 2 | 0 | |
| | | 0.4 | 0 | |
| Fenarimol | SC 125 g/l | 10 | 4 | |
| | | 2 | 0 | |
| Fenpropimorph | EC 750 g/l | 10 | 3 | |
| | | 2 | 0 | |
| | | 0.4 | 0 | |
| Flusilazole | WP 200 g/kg | 50 | 48 | |
| | | 10 | 26 | |
| | | 2 | 8 | |
| Prochloraz | EC 400 g/l | 10 | 48 | |
| | | 2 | 19 | |
| | | 0.4 | 8 | |
| Pyrifenox | WP 500 g/kg | 50 | 15 | |
| | | 10 | 8 | |
| | | 10 | 1 | |
| | | 2 | 0 | |
| | | 0.4 | 0 | |
| Spiroxamine | EC 500 g/l | 50 | 16 | |
| | | 10 | 5 | |
| | | 2 | 3 | |
| | | 0.4 | 0 | |
| BP-4 Cyproconazole | Tankmix | 10 + 10 | 9 | 1 |
| | | 2 + 2 | 10 | 4 |
| BP-4 Dinocap | Tankmix | 50 + 50 | 29 | 31 |
| | | 10 + 10 | 15 | 5 |
| | | 2 + 2 | 5 | 0 |
| | | 0.4 + 0.4 | 9 | 0 |
| BP-4 Fenarimol | Tankmix | 10 + 10 | 6 | 4 |
| | | 2 + 2 | 1 | 0 |
| BP-4 Fenpropimorph | Tankmix | 10 + 10 | 4 | 3 |
| | | 2 + 2 | 5 | 0 |
| | | 0.4 + 0.4 | 5 | 0 |
| BP-4 Flusilazole | Tankmix | 50 + 50 | 70 | 54 |
| | | 10 + 10 | 49 | 26 |
| | | 2 + 2 | 26 | 8 |
| BP-4 Prochloraz | Tankmix | 10 + 10 | 49 | 48 |
| | | 2 + 2 | 30 | 19 |
| | | 0.4 + 0.4 | 19 | 8 |
| BP-4 Pyrifenox | Tankmix | 50 + 50 | 26 | 25 |
| | | 10 + 10 | 10 | 8 |
| BP-4 Triadimefon | Tankmix | 50 + 50 | 29 | 20 |
| | | 10 + 10 | 10 | 5 |
| BP-4 Triadimenol | Tankmix | 50 + 50 | 46 | 21 |
| | | 10 + 10 | 19 | 1 |
| | | 2 + 2 | 3 | 0 |
| | | 0.4 + 0.4 | 1 | 0 |
| BP-4 Spiroxamine | Tankmix | 50 + 50 | 43 | 26 |
| | | 10 + 10 | 24 | 5 |
| | | 2 + 2 | 6 | 3 |
| | | 0.4 + 0.4 | 3 | 0 |

Example 17

Fungicidal Efficacy of the Mixture of Different Benzophenones+Metconazole (2 Day Curative) against *Blumeria graminis f. sp. tritici* on Wheat The tank mixes were obtained from technical material of the benzophenones BP-2 and BP-4 and metconazole. The benzophenones, the type of formulations, the observed and expected efficacies with different rates are given in Table XVII:

TABLE XVII

| Compound | Formulation | dose rate (ppm) | Observed Efficacy | Expected Efficacy |
|---|---|---|---|---|
| BP-2 | EC 100 g/l | 54 | 67 | |
| | | 18 | 25 | |
| | | 6 | 18 | |
| | | 2 | 13 | |
| | | 0.67 | 4 | |
| BP-4 | TC 100% | 54 | 92 | |
| | | 18 | 78 | |
| | | 6 | 42 | |
| | | 2 | 27 | |
| | | 0.67 | 9 | |
| Metconazole | EC 100 g/L | 27 | 40 | |
| | | 9 | 14 | |
| | | 3 | 7 | |
| | | 1 | 2 | |
| | | 0.33 | 0 | |
| BP-2 Metconazole | Tankmix | 27 + 54 | 90 | 80 |
| | | 9 + 18 | 67 | 35 |
| | | 3 + 6 | 46 | 23 |
| | | 1 + 2 | 22 | 12 |
| | | 0.33 + 0.67 | 9 | 4 |
| BP-4 Metconazole | Tankmix | 27 + 54 | 98 | 95 |
| | | 9 + 18 | 93 | 81 |
| | | 3 + 6 | 49 | 45 |

Example 18

Fungicidal Efficacy of the Mixture of BP-4+AP-4 (1 Day Residual) against *Ucinula nectator* on Vines The tank mixes were obtained from technical material of BP-4 and AP-4. The active ingredients, the type of formulations, the observed and expected efficacies with different rates are given in Table XVIII:

TABLE XVIII

| Compound | Formulation | dose rate (ppm) | Observed Efficacy | Expected Efficacy |
|---|---|---|---|---|
| BP-4 | TC 100% | 8 | 42 | |
| | | 4 | 43 | |
| | | 2 | 9 | |
| | | 1 | 28 | |
| | | 0.5 | 21 | |
| | | 0.25 | 0 | |
| AP-4 | TC 100% | 1 | 76 | |
| | | 0.5 | 76 | |
| | | 0.25 | 50 | |
| | | 0.12 | 32 | |
| | | 0.06 | 7 | |
| | | 0.03 | 13 | |
| BP-4 AP-4 | Tankmix | 8 + 1 | 88 | 86 |
| | | 4 + 0.5 | 91 | 87 |
| | | 2 + 0.25 | 85 | 79 |
| | | 1 + 0.12 | 89 | 83 |
| | | 0.5 + 0.06 | 88 | 81 |
| | | 0.25 + 0.03 | 79 | 76 |

B Field Tests

Example 19

Fungicidal Efficacy of the Mixture of BP-1+ Metconazole in the Field against the Sugar Beet Disease *Cercospora beticola*

The tank mix was obtained from a SC formulation containing 100 g of BP-1 per liter and a SL formulation containing 60 g of metconazole per liter. The observed and expected efficacies are given in Table XIX

TABLE XIX

| dose rate g/ha | | Observed | Expected |
|---|---|---|---|
| BP-1 | metconazole | Efficacy | Efficacy |
| 250 | 0 | 42.5 | — |
| 0 | 90 | 58 | — |
| 250 | 90 | 85.4 | 75.9 |

What is claimed is:

1. A fungicidal composition comprising a fungicidally acceptable carrier and/or surface active agent and synergistically effective amounts of
  (a) at least one benzophenone of formula IA

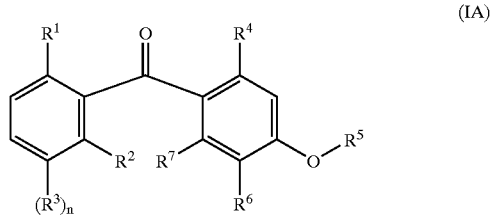

(IA)

wherein
  $R^1$ represents a halogen atom, a methyl, trifluoromethyl, methoxy or hydroxy group,
  $R^2$ represents a halogen atom or a methyl group,
  $R^3$ independently represents a halogen atom, an optionally substituted alkyl or alkoxy group or a nitro group;
  $R^4$ represents a halogen atom, a cyano, carboxy, hydroxy or nitro group or an optionally substituted alkyl, alkoxy, alkenyl, alkylthio, alkylsulphinyl, alkylsulphonyl or amino group;
  $R^5$ represents an optionally substituted alkyl group;
  $R^6$ represents a halogen atom or a nitro group, an optionally substituted alkyl, alkoxy, alkenyloxy, alkynyloxy, alkylthio, cycloalkyl, cycloalkoxy, aryloxy group;
  n is 0 or 1; and
  $R^7$ independently represents a halogen atom, an optionally substituted alkyl, alkenyl, alkynyl, alkoxy, alkenyloxy, alkynyloxy, cycloalkyl, cycloalkoxy group;
  (b) at least one fungicidally active ingredient (D) selected from the group consisting of acibenzolar, benomyl, captan, carboxin, chlorothalonil, copper, cyprodinil, dinocap, dithianon, dimethomorph, dodine, ethirimol, famoxadone, fenpiclonil, fluazinam, mancozeb, metalaxyl, pyrifenox, quinoxyfen, sulfur and vinclozolin.

2. A composition according to claim 1, wherein the benzophenone of formula IA is selected from the group consisting of
  6'-butoxy-2,6-dichloro-4',5'-dimethoxy-2'-methylbenzophenone;
  2,6-dichloro-4',5'-dimethoxy-6'-(2-fluorobenzyloxy)-2'-methylbenzophenone;
  6'-benzyloxy-4',5'-dimethoxy-2,6-dimethyl-2'-methylbenzophenone;
  5-bromo-2',6-dimethyl-2,4',5',6'-tetramethoxybenzophenone; and
  2,6-dichloro-2'-methyl-4',5',6'-trimethoxybenzophenone.

3. A composition as claimed in claim 1, which comprises one compound of formula IA and two different fungicidally active ingredients (D).

4. A composition as claimed in claim 1, wherein the ratio (by weight) of the benzophenone of formula IA to the fungicidally active ingredient (D) is from 10:1 to 1:10.

5. A composition as claimed in claim 1, wherein the ratio (by weight) of the benzophenone of formula IA to the fungicidally active ingredient (D) is from 5:1 to 1:5.

6. The composition defined in claim 1, wherein the benzophenone of formula IA is 5-bromo-2',6-dimethyl-2,4',5',6'-tetramethoxybenzophenone.

7. The composition defined in claim 1, wherein the at least one fungicidally active ingredient (D) is selected from the group consisting of captan, chlorothalonil, copper, cyprodinil, dinocap, dithianon, dimethomorph, dodine, ethirimol, famoxadone, fenpiclonil, fluazinam, mancozeb, metalaxyl, pyrifenox, quinoxyfen and sulfur.

8. The composition defined in claim 7, wherein the benzophenone of formula IA is 5-bromo-2',6-dimethyl-2,4',5',6'-tetramethoxybenzophenone.

9. Method of controlling the growth of fungi at a locus which comprises applying a composition as claimed in claim 1 to the locus.

10. Method of controlling the growth of powdery mildew at a locus which comprises applying a composition as claimed in claim 1 to the locus.

11. The method of claim 9, wherein the benzophenone of formula IA is selected from the group consisting of
  6'-butoxy-2,6-dichloro-4',5'-dimethoxy-2'-methylbenzophenone;
  2,6-dichloro-4',5'-dimethoxy-6'-(2-fluorobenzyloxy)-2'-methylbenzophenone;
  6'-benzyloxy-4',5'-dimethoxy-2,6-dimethyl-2'-methylbenzophenone;
  5-bromo-2',6-dimethyl-2,4',5',6'-tetramethoxybenzophenone; and
  2,6-dichloro-2'-methyl-4',5',6'-trimethoxybenzophenone.

12. The method of claim 9, wherein the benzophenone of formula IA is 5-bromo-2',6-dimethyl-2,4',5',6'-tetramethoxybenzophenone.

13. The method of claim 9, wherein the at least one fungicidally active ingredient (D) is selected from the group consisting of captan, chlorothalonil, copper, cyprodinil, dinocap, dithianon, dimethomorph, dodine, ethirimol, famoxadone, fenpiclonil, fluazinam, mancozeb, metalaxyl, pyrifenox, quinoxyfen and sulfur.

14. The method of claim 13, wherein the benzophenone of formula IA is 5-bromo-2',6-dimethyl-2,4',5',6'-tetramethoxybenzophenone.

* * * * *